(12) United States Patent
Aita

(10) Patent No.: US 7,103,209 B1
(45) Date of Patent: Sep. 5, 2006

(54) METHOD FOR EXTRACTING OBJECTIVE IMAGE

(75) Inventor: Kazuo Aita, Chiba (JP)

(73) Assignee: SII NanoTechnology Inc., (JP)

( * ) Notice: Subject to any disclaimer, the term of this patent is extended or adjusted under 35 U.S.C. 154(b) by 743 days.

(21) Appl. No.: 10/130,881

(22) PCT Filed: Nov. 20, 2000

(86) PCT No.: PCT/JP00/08191

§ 371 (c)(1),
(2), (4) Date: Jul. 22, 2002

(87) PCT Pub. No.: WO01/41067

PCT Pub. Date: Jun. 7, 2001

(30) Foreign Application Priority Data

Nov. 29, 1999 (JP) ................................ 11-338484

(51) Int. Cl.
*G06K 9/00* (2006.01)

(52) U.S. Cl. ...................... 382/144; 382/199; 382/205; 250/553; 250/559.3

(58) Field of Classification Search ................ 382/144, 382/181, 209, 237, 252, 270, 199, 176, 261, 382/232, 162, 205; 358/1.9, 296, 3.01, 3.14; 250/553, 559.3
See application file for complete search history.

(56) References Cited

U.S. PATENT DOCUMENTS

| | | | | |
|---|---|---|---|---|
| 4,908,872 A | * | 3/1990 | Toriu et al. .................. | 382/197 |
| 5,887,080 A | * | 3/1999 | Tsubusaki et al. .......... | 382/172 |
| 6,282,309 B1 | * | 8/2001 | Emery ......................... | 382/145 |
| 6,396,943 B1 | * | 5/2002 | Yamashita ................... | 382/144 |
| 6,697,497 B1 | * | 2/2004 | Jensen et al. ................ | 382/100 |

* cited by examiner

*Primary Examiner*—Sheela Chawan
(74) *Attorney, Agent, or Firm*—Adams & Wilks

(57) ABSTRACT

Noted portions of an image, such as a pin point hole in an isolated area or a pattern contour that forms a continuous boundary area, are clearly displayed by first erasing background noise by acquiring information regarding differences between an image detection signal (pixel) of each scanned position (dot) in matrix form and image detection signals of the surrounding scanned positions, and secondly, by adopting a value that is either a largest or smallest value greater than or equal to zero among a plurality of sets of information on value differences as new image information for the scanned position.

6 Claims, 3 Drawing Sheets

5 PIN POINT HOLE

5
PIN POINT HOLE

METHOD FOR EXTRACTING OBJECTIVE IMAGE

TECHNICAL FIELD

The present invention relates to image processing technology for extracting noted images constituting part of an image recognized as matrix-shaped pixel information, and particularly relates to a noted image extraction method effective in repairing semiconductor chip photomasks.

BACKGROUND ART

When shielding material becomes adhered to a photomask (black defect 1) used for the production of semiconductor circuit elements or when any part of the photomask is missing (white defect 2) as shown in FIG. 2, semiconductor circuit elements cannot be produced as designed. A practical method for repairing such defects is to perform assist deposition or etching on the defects using a focused ion beam. However, the mask cannot be repaired with high precision if the position of the defect cannot be identified accurately. To achieve high precision, it would be necessary, first of all, to gain an accurate recognition of the reference position (pin point hole 5) set in the mask to minimize the difference between the contour recognition of pattern 3 and the drift, and secondly, to accurately recognize the actual contour of mask pattern 3 shaped on the substrate as a position relative to the pin point hole 5. The condition of the mask is then observed by acquiring a microscopic view of the mask using a microscope such as a scanning ion microscope. The displayed image of the pattern contour may drift significantly from the actual image, depending on which threshold value is used to recognize the boundary between the pattern contour and the substrate. FIG. 3A shows the sectional view of the boundary of pattern 3 on a glass substrate 4. FIG. 3B shows an example of these secondary electron detection signals. For example, as shown in FIG. 3B1, the pattern contour image varies considerably (between contour position a1 and a2) depending on whether the threshold value used for comparing with the secondary ion detection quantity is set to be high $1_1$, or low $1_2$. In the case of pattern 3, it is desirable to recognize the boundary by detecting the shoulder portion of the shielding material such as chrome. However, it is difficult to set an appropriate threshold value $1_1$ in cases, for example, where a background component BG within the signal is large and the signal difference between the substrate area and the shielding material area is small, as shown in FIG. 3B2. In addition, since the background component is not constant and changes depending on place and time, there may be cases where the pattern cannot be recognized because the threshold value $1_3$ is set to be higher than the pattern area signal, or on the contrary, when the glass substrate area is also recognized as a part of the pattern area because the threshold value is set to be lower than the pattern area signal, as a result of the varying influence of the background component. Moreover, since there are problems with the position of the boundary shifting in both cases where detected secondary ions are taken to be part of the substrate-side substance and cases where the secondary ions detected are taken to be part of the blocking material, detection of a shoulder portion of a blocking material such as chrome, etc. so as to confirm a boundary for precise displaying is not straightforward.

A differential processing method has been applied as a related method for emphasizing the contour to distinguish this boundary line. However, in this method, small signal fluctuations that do not correspond to the boundary may also be included as the subject of differential processing and the peak level as a result may become unnecessarily large, making after treatment troublesome. For this reason, this method cannot necessarily be considered as the most appropriate means of processing.

The object of the present invention is to solve the problems encountered in the related technology described above i.e. to provide a technology to accurately recognize and display the boundary between the substrate and the shielding material on the photomask that will in turn allow for high precision repair of defects on the photomask conducted based on accurate recognition of the position of this boundary.

SUMMARY OF THE INVENTION

The present invention is an image processing method for clearly displaying specific noted portions of an image such as a pin point hole in an isolated area and/or a pattern contour that forms a continuous boundary area, by first, erasing the background noise by acquiring information regarding differences between an image detection signal (pixel) of each scanned position (dot) in matrix form and image detection signals of surrounding scanned positions, and secondly, by adopting a value that is either a largest or smallest value equal to or greater than zero among a plurality of sets of information for differences as new image information for the scanned position.

DETAILED DESCRIPTION OF THE INVENTION

When a microscopic image of a mask is obtained using equipment such as a scanning ion microscope, the image is frequently smoothened out at first as a preliminary treatment of the image by gaining the mean of the surrounding values, since random noise is usually overlapping the pixel signals that have been initially detected for each dot on the matrix. By implementing this smoothing process, the image that will be obtained will normally be smoother with limited unevenness. The peak level is then measured using this smoothened image. For the purpose of facilitating the understanding of the image processing principles applied in the present invention, one matrix zone for indicating each scanned position shall be considered to be equivalent to the diameter of the focused ion beam. When a pin point hole 5 indicates a reference position, it shall be understood that the detection signal can be represented by a one dot signal as shown in FIG. 1A, because pin point hole 5 is a small isolated area with a surrounding shape with an exposed glass substrate and with a further smaller sub-area covered with shielding material existing in the center.

Figure 1:
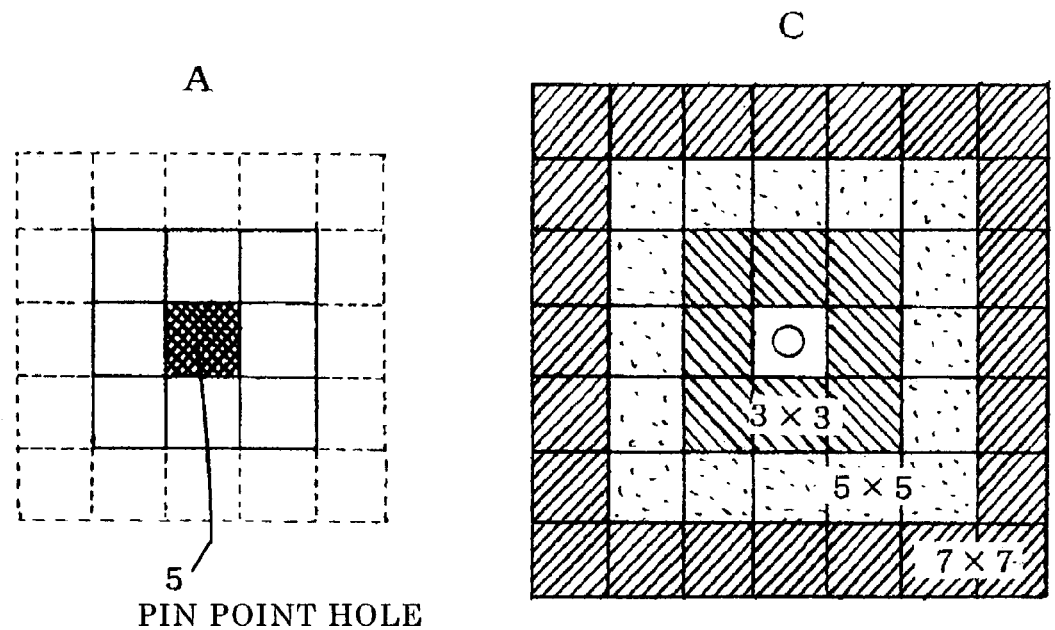
FIG. 1 is a view illustrating pin point holes and the pattern on the pixel matrix and the state of the surrounding dots.
Figure 1:
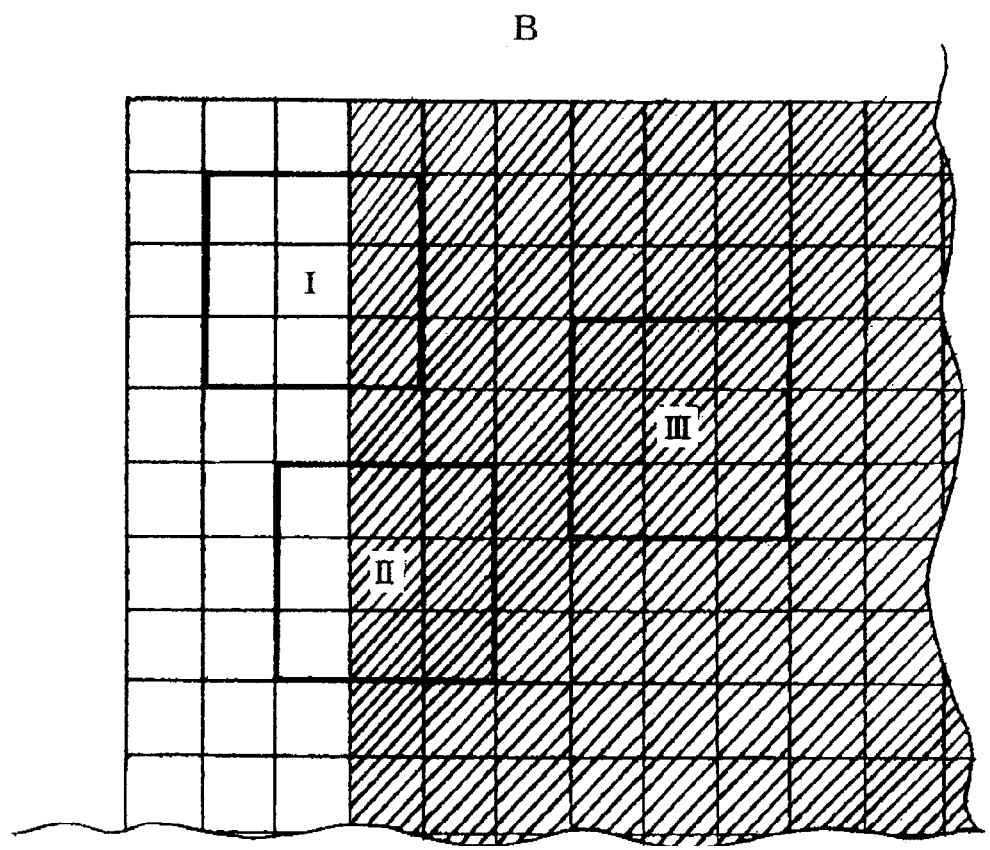
Figure 2:
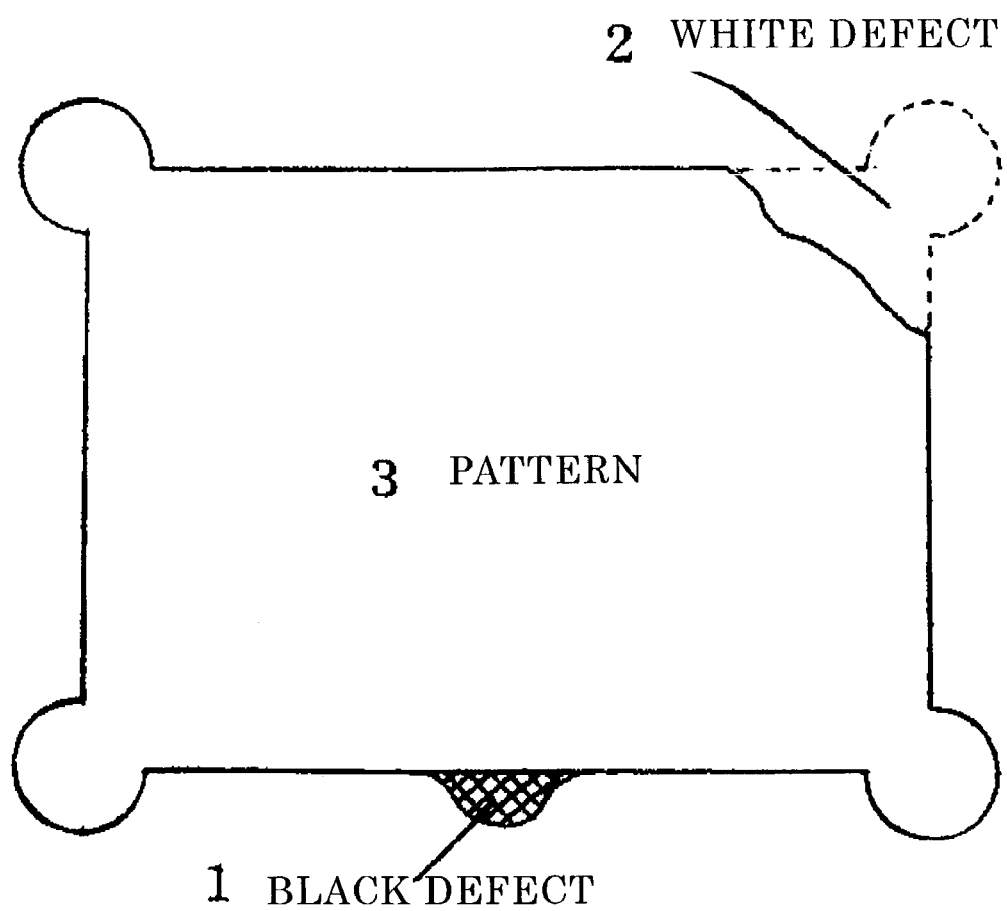
FIG. 2 is a view illustrating white defects and the black defects on a photomask.
Figure 3:
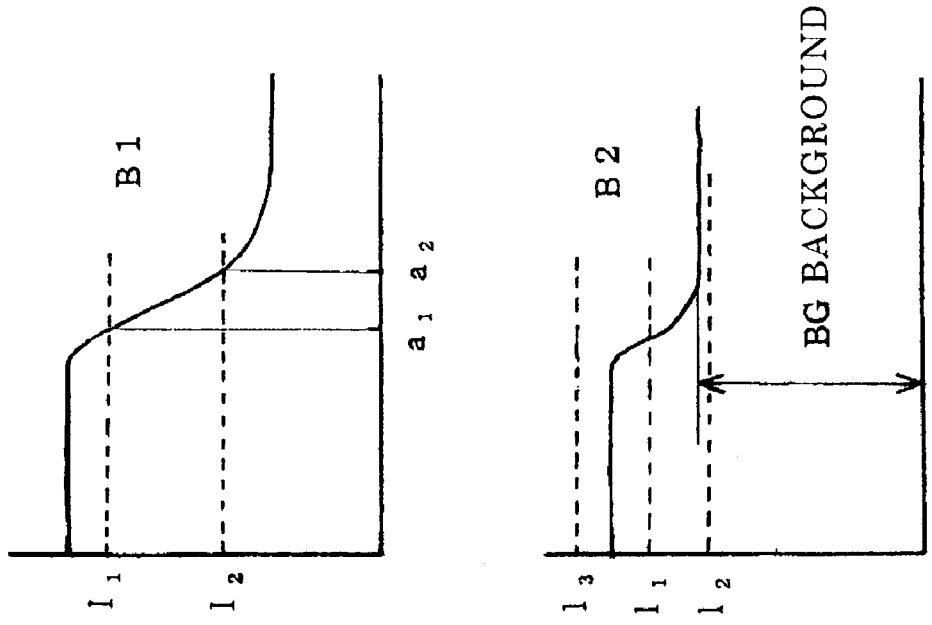
FIG. 3 is a view showing a cross-section and image signals for the pattern boundary area.
Figure 3:
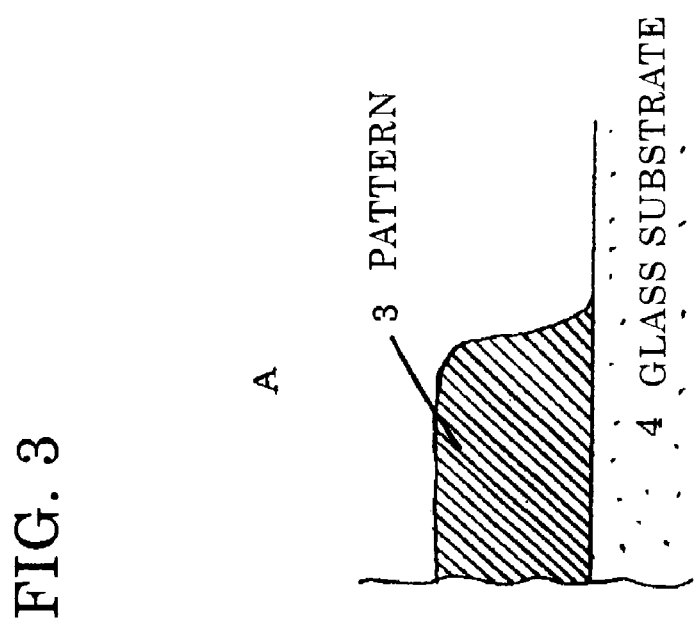

When the pattern boundary is a straight line, it shall be understood that the detection signal can be represented by a dot signal map because the area where the shielding material exists and the area where the glass substrate is exposed will appear in a shape resembling a continuous uni-directional bank as shown in FIG. 1B. First of all, the difference between the detected values for the central dot and the surrounding 8 dots of the nearest 3×3 dot area as shown in FIG. 1A is calculated. When the pin point hole 5 is at the center, the difference between this dot and the other 8 dots will all be large because the pin point hole 5 is an isolated one dot area. However, when the pattern boundary is included in this 3×3 dot area, the difference between the detected signal value for this dot and that of the surrounding dots should vary respectively, with some being larger or smaller than others.

If the smallest value equal to or greater than zero among the 8 difference values is adopted as the new value for this dot, this value will be close to zero when a signal of the same level as the central dot is present in the surroundings, and will become large only when there is no signal of the same level as the central dot existing in the surroundings. Therefore, the new image obtained from this processing method will appear with only the small isolated area remaining as with A shown in FIG. 1A, and in respect of the pattern area, a boundary resembling a continuous uni-directional causeway as shown in I and II of FIG. 1B will appear with the central area erased from the image because the signal detected from here is a low-level, as shown in III of FIG. 1B. As a result, only pin point hole 5 that indicates the reference position will appear clearly on the image. This processing method that allows the obtained image to show only the pin point hole 5 without the pattern area 3 is a suitable image processing method in the current situation where it is difficult to focus the reference position in a larger setting for semiconductor integrated circuits with patterns of higher density.

Moreover, if the largest value greater than or equal to zero among the 8 difference values is adopted as the new value of this dot, this value will be large when a signal of a level that is different from the central dot is present in the surroundings, and will become small only when there is no signal of a level that varies from the signal level of the central dot existing in the surroundings. Therefore, in the image obtained through this processing method, the pin point hole that appears as a small isolated area as shown in FIG. 1A is displayed in a form expanded with respect to the surrounding dots, and the pattern boundary resembles a continuous uni-directional bank as shown in I and II of FIG. 1B remains as a line that is 2-dots wide, with the internal parts of the pattern being erased in the way shown in III of FIG. 1B due to all having a level detected to be the same as in the surroundings. In other words, this will be the case where the contour of the boundary area of pattern 3 will appear as a line while point 5 will be displayed in an expanded form. The present invention is significant for erasing background noise that changes according to the detecting position and time beforehand by adopting the value obtained from the calculation of the difference with the surrounding pixels as a reference value. Further, because the peak level is obtained as a value relative to the values obtained from the surrounding pixels instead of as the absolute value obtained from the image detected initially, the S/N ratio will be higher and the setting of the threshold value will become easier.

In order to simplify the description of the image processing principle applied in this present invention, the above description has been written on the assumption that the size of one dot is approximately the same as the diameter of the focused ion beam. In practice, more detailed scanning can be implemented. However, in that case, the signals detected from the adjacent dots will not differ greatly, since many beam spots will become common. As a result, the calculation of the adjacent 3×3 dot area will, technically speaking, be less significant for use as data for comparison. Moreover, the calculation of the dots that are farther away than the beam diameter will also not be that technically significant for use as the data for comparison, since their correlation with the pixel information will be lower. Therefore, pixels positioned one diameter of the beam away will be suitable for use as the dots for comparison, which means that it would be most appropriate to select, for example, a 5×5 or 7×7 dot area that is at the position of a beam diameter away as the surrounding dot area. As shown in FIG. 1C, 16 sets of value differences will result from the calculation using the 5×5 dot area, and 24 sets will result from the 7×7 dot area. Moreover, the above description only takes into account the microscopic image obtained from the scanning ion microscope using the focused ion beam. However, this is just one example and the present invention can be applied to images obtained from electronic or optical microscopes, provided that the image is composed of information on pixels in matrix form.

FIRST EMBODIMENT

Next, an example is shown for a case where the processing is not based on simple calculation of difference with the surrounding dots. In this example, the difference between the value obtained from the focused dot and the mean value of the dots lined uni-directionally at both sides of the focused dot set as the center is calculated. The distance between the dots is likewise assumed to be approximately the same as the beam diameter. In the case of a 3×3 dot area, four sets of value differences (horizontal, vertical, left diagonal, right diagonal) will result from calculations using this area. There are eight sets when a 5×5 dot area is used, and twelve sets when a 7×7 dot area is used. The result of this calculation implicitly shows that the values will be small when the signals do not vary in one direction or change continuously (increases or decreases in a unitary manner), and will be large when the signal values form a curve with a peak level somewhere therebetween. In this case, the value obtained from a very small isolated area such as the pin point hole will be large in all directions. In regard to the pattern boundary area resembling the shape of a uni-directional bank, the values obtained from the dots lined in the direction of crossing the bank will be large, and the values from the dots lined along the bank will be small. When the smallest value greater than or equal to zero among the plurality of sets of values is adopted as the new information for this dot, the value for the pin point hole will be relatively large even when the smallest value is adopted since the value difference will be large in all directions. However, in regard to the pattern, the values obtained at the boundary area will be small since the values along the bank will be small. Furthermore, the values obtained at the central section will also be small since they will be continuously small in all directions. Therefore, the image obtained from this processing method will only display the pin point hole. Moreover, in case the largest value (above zero) among the plural sets of values is adopted as the new information of the dot being noted, the value of the pin point hole will be relatively large since it will be a large value in all directions. In regard to the pattern, the values obtained at the boundary area that are lined in the direction crossing the causeway will be large. On the other hand, the values obtained at the central section will be small since they will be continuously small in all directions. As a result, the pattern contour will be displayed in linear form on the image.

SECOND EMBODIMENT

The following is another example of a case where processing is not based on simple calculation of differences with the surrounding dots. In this example, the difference between the absolute value obtained from the difference of the mean value of the dots lined up uni-directionally on both sides of the focused dot set at the center and the mean value of the dots on both sides lined perpendicularly to the uni-drectionally lined dots and the value of the focused dot is calculated. The distance between the dots has been assumed likewise to be about the same as the beam diameter. In the case of a 3×3 dot area, two sets of value differences (horizontal, vertical, left diagonal, right diagonal) will result from this calculation using this area.

In the case of a 5×5 dot area, there will be four sets of value differences resulting, and 6 sets when a 7×7 dot area is used for the calculation. The result of the calculation will implicitly show that the calculated value will be small when there is a difference in the way the signals change in the orthogonal direction. Therefore, the value obtained from a very small isolated area like the pin point hole will be large when there is no difference in the way the signals change in all directions. Regarding the pattern boundary area resembling the shape of a uni-directional causeway, the calculation of the values obtained from the dots lined up along the bank and the values obtained from the dots lined up perpendicularly to the dots lined up along the bank in an orthogonal direction will be large, and the values obtained from other calculations will be small. When the smallest value (above zero) among the plurality of sets of values is adopted as the new information for the noted dot, the value of the pin point hole will be relatively large even when the smallest value is adopted since the value difference will be large in all directions. However, regarding the pattern, the values obtained at the boundary area will be small since the values along the causeway will be small. Furthermore, the values obtained at the central section will also be small since they will be continuously small in all directions. Therefore, the image obtained from this processing method will only display the pin point hole. Moreover, when the largest value equal to or greater than zero among the plurality of sets of values is adopted as the new information for the noted dot, the value of the pin point hole will be relatively large since it will be a large value in all directions. Regarding the pattern, the values will be large since the calculation of the values obtained for the dots at the boundary area that are lined up along the causeway and the values obtained for the dots lined up perpendicularly to the dots lined along the bank will be large. On the other hand, the values obtained at the central section will be small since they will be continuously small in all directions. As a result, the pattern contour will also be displayed in linear form on the image obtained from this processing method.

The present invention basically takes into account of the calculation of the difference between the information for each dot and the signal information for the surrounding dots. However, the calculated information that it takes into account is not necessarily limited to the calculations exemplified above. For example, instead of the signal information obtained from the values lined up uni-directionally, the largest or the smallest value (above zero) difference between the mean value of two values obtained for two surrounding dots that are positioned relatively with respect to the position of a specific angle and the value obtained for the dot concerned can also be adopted.

Since the present invention is an image processing method to clearly display specific noted portions of an image such as a pin point hole in an isolated area or a pattern contour which forms a continuous boundary area by first erasing background noise by acquiring information on the difference between image detection signals for each dot in matrix form and image detection signals for surrounding dots, and by secondly adopting a value that is either the largest or the smallest value greater than or equal to zero among a plurality of sets of information on value differences as the new image information of the noted dot, images processed by this method will not be affected by the values obtained from background elements that vary depending on the time and position of image processing since these elements will be erased from the image, and will also provide ease in setting strict threshold values. Moreover, since the pattern area will be erased from the image when the smallest value greater than or equal to zero is adopted from the plurality of sets of information on value differences, a pin point hole constituting a reference point will become easier to identify. This feature that the pin point hole will become easier to identify because the pattern area near the pin point hole will be erased from the image is effective in particular with recent semiconductor circuits that are increasingly becoming more densely integrated.

The invention claimed is:

1. A noted image extraction method in image processing technology of an image recognized as matrix-shaped pixel information, the method comprising:
    obtaining a difference information between an image detection signal of the noted portion and image detection signals for surrounding scanned positions as an image signal for each scanned position, wherein difference information for differences between image detection signal values for each scanned position and surrounding scanned positions is obtained by subtracting image detection signal values for surrounding scanned positions from image detection signal values for each scanned position; and
    adopting a smallest value of greater than or equal to zero among the set of values resulting from the calculation of differences as the value for recognizing a pin point hole in an isolated area and adopting a largest value of greater than or equal to zero among the set of values resulting from the calculation of differences as the value for recognizing a pattern contour of a continuous pattern area.

2. A noted image extraction method according to claim 1; wherein a distance between each scanning position used in difference information calculation and a surrounding scanned position is taken to be the scanning beam diameter, with the image being a charged particle scanning microscope image.

3. A noted image extraction method in image processing technology of an image recognized as matrix-shaped pixel information, the method comprising:
    obtaining a difference information between an image detection signal of the noted portion and image detection signals for surrounding scanned positions as an image signal for each scanned position, wherein difference information for differences between image detection signal values for each scanned position and surrounding scanned positions is obtained by subtracting mean values for image detection signal values for surrounding scanned positions at both sides of each scanned position from image detection signal values for each scanned position; and adopting a smallest value of greater than or equal to zero among the set of values resulting from the calculation of differences as the value for recognizing a pin point hole in an isolated area and adopting a largest value of greater than or equal to zero among the set of values resulting from the calcuation of differences as the value for recognizing a pattern contour of a continuous pattern area.

4. A noted image extraction method according to claim 3; wherein a distance between each scanning position used in difference information calculation and a surrounding scanned position is taken to be the scanning beam diameter, with the image being a charged particle scanning microscope image.

5. A noted image extraction method in image processing technology of an image recognized as matrix-shaped pixel information, the method comprising:

obtaining a difference information between an image detection signal of the noted portion and image detection signals for surrounding scanned positions as an image signal for each scanned position, wherein difference information for differences between image detection signal values for each scanned position and surrounding scanned positions is obtained by subtracting absolute values of differences between mean values of image detection signal values for surrounding scanned positions at both sides of each scanned position and mean values of image detection signal values obtained from the surrounding scanned positions at both sides that run perpendicularly to the surrounding scanned positions at both sides of each scanned position from image detection signal values for each scanned position; and adopting a smallest value of greater than or equal to zero among the set of values resulting from the calculation of differences as the value for recognizing a pin point hole in an isolated area and adopting a largest value of greater than or equal to zero among the set of values resulting from the calcuation of differences as the value for recognizing a pattern contour of a continuous pattern area.

6. A noted image extraction method according to claim 5; wherein a distance between each scanning position used in difference information calculation and a surrounding scanned position is taken to be the scanning beam diameter, with the image being a charged particle scanning microscope image.

* * * * *